(12) United States Patent
van der Kaap et al.

(10) Patent No.: US 9,121,005 B2
(45) Date of Patent: Sep. 1, 2015

(54) METHODS AND APPARATUS FOR HANDLING MICROBIAL SAMPLES

(75) Inventors: Trienko Marten van der Kaap, Drachten (NL); Martijn Kleefstra, Dokkum (NL); Ingeta Marie Sofie Edlund Tjernberg, Lomma (SE); Jetze Botma, Drachster Campagnie (NL)

(73) Assignee: BD Kiestra B.V. (NL)

( * ) Notice: Subject to any disclaimer, the term of this patent is extended or adjusted under 35 U.S.C. 154(b) by 687 days.

(21) Appl. No.: 12/740,746

(22) PCT Filed: Nov. 4, 2008

(86) PCT No.: PCT/NL2008/050693
§ 371 (c)(1), (2), (4) Date: Sep. 13, 2010

(87) PCT Pub. No.: WO2009/061183
PCT Pub. Date: May 14, 2009

(65) Prior Publication Data
US 2010/0330654 A1    Dec. 30, 2010

(30) Foreign Application Priority Data
Nov. 5, 2007    (EP) ..................................... 07119955

(51) Int. Cl.
*C12M 1/36*    (2006.01)
*C12M 1/30*    (2006.01)

(52) U.S. Cl.
CPC ........... *C12M 33/02* (2013.01); *Y10T 428/2982* (2015.01)

(58) Field of Classification Search
None
See application file for complete search history.

(56) References Cited

U.S. PATENT DOCUMENTS

| | | | |
|---|---|---|---|
| 3,623,958 A * | 11/1971 | Fitzgerald | 435/243 |
| 3,660,243 A | 5/1972 | Young | |
| 3,830,701 A | 8/1974 | Stussman | |
| 5,562,870 A * | 10/1996 | Bonin | 264/8 |
| 6,755,588 B1 * | 6/2004 | Tsujikura | 401/215 |
| 2006/0211080 A1 * | 9/2006 | Frost et al. | 435/30 |

FOREIGN PATENT DOCUMENTS

| | | |
|---|---|---|
| EP | 1340810 | 9/2003 |
| WO | WO 2006112771 A1 * | 10/2006 |

OTHER PUBLICATIONS

Shiho, et al., Magnetic compounds as coatings on polymer particles and magnetic properties of the composite particles, Journal of Materials Chemistry, 2000, vol. 10, 333-336.*
Millan et al., Particle Size and Density Control in Magnetic Polymer Nanocamposites, Material Research Society Symposium Proceeedings, vol. 733E, pp. T5.2.1-T5.2.6.*
Gijs, M., Magnetic bead handling on-chip: new opportunities for analytical applications, Microfluid Nanofluid, 2004, vol. 1, pp. 22-40.*
Nishimoto et al., The Effect of Titanium Surface Roughening on Protein Absorption, Cell Attachment, and Cell Spreading, The International Journal of Oral & Maxillofacial Implants, 2008, vol. 23, pp. 675-680.*

* cited by examiner

*Primary Examiner* — Thane Underdahl
*Assistant Examiner* — Christopher Keller
(74) *Attorney, Agent, or Firm* — Lerner, David, Littenberg, Krumholz & Mentlik, LLP

(57) ABSTRACT

This invention pertains to the general field of microbiology, and more specifically to transfer, inoculation and/or streaking of micro-organisms, e.g. for the purpose of obtaining individual colonies. Provided is a method for streaking a microbial sample onto a solid carrier, comprising the steps of: a) contacting at least one ferromagnetic particle with a solid carrier, followed or preceded by providing the particle with at least part of said sample, and b) applying a magnetic field gradient to allow for magnetically controlled motion of said particle on said surface, such that at least part of the sample is streaked onto the solid carrier. Also provided is an apparatus for carrying out such method in an (semi-)automated fashion.

22 Claims, 5 Drawing Sheets

METHODS AND APPARATUS FOR HANDLING MICROBIAL SAMPLES

RELATED APPLICATIONS

This application is the United States National Stage of International Application No. PCT/NL2008/050693, filed Nov. 4, 2008, which was published as International Publication No. WO 2009/061183, and which claims benefit of European Patent Application No. 07119955.8 filed Nov. 5, 2007. Both applications are incorporated by reference in their entirety herewith.

This invention pertains to the general field of microbiology, and more specifically to transfer, inoculation and/or streaking of microorganisms, e.g. for the purpose of obtaining individual colonies. Among others, it relates to methods for handling and streaking microbial specimens and to a (semi-) automated apparatus to prepare specimens for visual counting, typing and other analysis of bacterial populations, for example in diagnostic microbiology.

One of the many procedures, which must be performed in microbiology, is plate streaking with the purpose of isolating microbiological colonies. The isolated colonies are absolutely necessary for the observance of colony morphology and for the performance of staining and other procedures that are necessary for determining the genus and in many cases, the species, strain, etc. of an unknown organism. In the classic technique, known as streaking, a sterile loop is first brought into contact with the sample or inoculum whose cells one wishes to transfer; it is then brought into contact with the plate containing sterile solid medium to which one wishes to transfer the cells, and is moved back and forth over the surface of a portion (e.g. one quarter) of the fresh plate. In the initial step, millions of cells may be transferred to the new plate, and must be further diluted by many orders of magnitude so that individual colonies, rather than confluent growth, will be obtained. Since the loop surface is also now contaminated with many thousands of cells, it must be either resterilized (e.g., by flame sterilization in the case of wire loops), or substituted by a new sterile loop (e.g. in the case of single-use, disposable plastic loops). The sterile loop is then brought into contact with the surface of the fresh plate which has been previously streaked, e.g. by several movements across the zone of the first streaking, and then another portion of the plate (e.g. a quarter of the plate adjacent to the first streaking) is streaked. This results in additional dilution of the cells. The loop is then either resterilized or replaced, is brought into contact with the second streaking area, and then a third zone of the plate is streaked. This process must be performed at least three or four times in order to be certain of obtaining individual colonies, rather than confluent growth, following incubation of the fresh plate.

The testing of clinical microbial specimens typically requires the streaking of several (e.g. 2 to 6) plates per test specimen. The manual streaking process requires approximately 30 seconds per agar plate of a skilled technologist's time. The quality of the streak and therefore the degrees of isolation of the micro-organism depends upon the training received by the technologist and the care taken in performing the process.

Thus, the manual inoculation and streaking process is very labour-intensive and time-consuming. Furthermore, in many diagnostic settings, such as a hospital microbial laboratory, there is often a peak load of samples coming in to be tested. It is not uncommon that the processing of up to a 1000 individual clinical samples of various types must be accomplished in a time window of only a few hours, typically at the end of a normal working day, like between 3 and 5 μm. This puts an enormous time pressure on the employees, equipment and laboratory space involved. The inoculation and streaking is however only the beginning of the actual microbial testing, and peak loads are also encountered for downstream procedures, including plate incubation, processing (e.g. staining) and the final plate assessment.

Therefore, there have been attempts in the field to automate the plate inoculation and/or streaking process.

For example, the ISOPLATER 180 (Vista Technology Inc., Edmonton, Alberta, Canada) is an automated Petri dish streaker. The machine automatically rotates the load carousel to bring in a stack of plates, downloads a dish, removes the lid, orients the dish, transfers the dish with its lid, streaks in four successive quadrants for isolation, replaces the lid and uploads the completed dish into the unload carousel. Spreading over the entire surface of an agar plate is accomplished by four individual nichrome loops which are sterilized by electrical heating between dishes.

WO2005/071055 discloses a streaker device and apparatus for streaking a microbial inoculum for single colonies on the surface of a solid growth medium. The device is characterized by a "comb-like" structure consisting of a row of spaced apart contact surfaces that are resiliently supported by a common support member. The streaking device is applied to the surface of an agar plate and is rotated to various degrees. Prior art dating back to the early eighties discloses streaking systems comprising the use of a spherical, magnetic metal particle, in particular steel balls. For instance, U.S. Pat. No. 3,830,701 describes a method and an apparatus for streaking a microbial sample comprising the contact of a stainless steel ball with an inoculum and generating a controlled motion of the ball using a moving magnet to transfer the microbial sample to a culture surface. U.S. Pat. No. 3,660,243 and U.S. Pat. No. 3,623,958 disclose methods and devices comprising similar features.

The systems known in the art will automate and replace many of the manual tasks traditionally involved in the inoculation and streaking of standard agar plates. However, they do not accommodate all of the user's preferences. These include: a) production of single colonies when using miniaturized or split plates; b) no cross-contamination; c) ease of use; d) large capacity (preferably at least 500 plates/hour); e) low cost and f) compatibility with different specimen types, e.g. liquid samples, swabs etc. and non-standard plates, such as split-plates.

The present inventors set out to address at least some of the above preferences in an attempt to provide further improved methods and apparatus for (semi-) automated handling of a microbial sample. They observed that the steel particles employed in the magnetically controlled streaking methods known in the art are unsuitable for reliable, high-speed automated streaking that is sought for today. In particular, it was found that the steel balls known in the art display insufficient rolling to achieve a good spreading of the inoculum onto a (culture) surface. At the high streaking rates desired nowadays (at least 500 plates/hour), the steel particles were ineffective to yield single colonies, especially when more complex streaking patterns were required to obtain a sufficient streaking path length on a limited surface area, e.g. the zigzag pattern with sharp bends to streak samples on split plates. Without wishing to be bound by theory, it is believed that a homogenous, non-composite steel particle forms a dipole and thus acts as a magnet itself. As a result, the steel particle "slips" on the surface of the plate during magnetically controlled motion and the particle cannot make optimal rolling movements.

It was surprisingly discovered that much better streaking results could be obtained when a non-homogenous, composite magnetic particle is used instead of the homogenous stainless steel particles known in the art. Furthermore, other particle characteristics such as diameter, density and/or surface roughness were identified as relevant for spreading performance of the particle. As is exemplified herein below, it was found that contacting a sample with a magnetic composite particle, such as a magnetic bead comprising both a magnetic and a non-magnetic material, allows for a very efficient and easy transfer of various types of samples from one carrier to another, e.g. from a urine collection tube or swab to a broth, a Petri dish or a microscopic glass slide. Furthermore, it was surprisingly observed that a microbial sample can be spread onto a solid surface or homogenized in a liquid medium by the motion of the magnetically controlled composite particle. The spreading onto a solid growth medium by placing a magnetic field under it produced more single, isolated microbial colonies when compared to manual streaking, even at high speed. A predetermined streaking pattern can be obtained with optimal usage of the surface area of a plate. The total path length of a streak can thus be increased within the confines of the plate. This obviates the need to switch to a larger size, and more expensive, culture plate. Of course, the longer the streak path length, the better the chance that an inoculum is sufficiently diluted to obtain isolated colonies. An optimal utilization of the plate surface area is especially advantageous when using miniaturized plates or so-called split plates having two different media contained in separate compartments of a single plate.

A further advantage of the magnetically controlled streaking as provided herein is that it can maximally accommodate surface variation. In contrast to the machine-held streaking devices known in the art, the magnetic particle used for sample transfer or streaking is not mechanically restrained in any fashion. It can therefore smoothly follow any surface without the risk of damaging the surface of e.g. a solid growth medium.

The invention therefore provides a method for transfer of a microbial sample, preferably a liquid sample, from a first carrier to a second carrier, said "transfer method" comprising the steps of:
 a) contacting at least part of said sample associated with said first carrier with at least one ferromagnetic particle, the particle being a spherical composite bead; and
 b) applying an external magnetic field gradient to allow for magnetically controlled motion of said bead, such that at least part of the sample is transferred to said second carrier.

Also provided is a method for streaking a microbial sample onto a solid carrier, said "streaking method" comprising the steps of:
 a) contacting at least one ferromagnetic particle with a surface of the solid carrier, the particle preferably being a spherical composite bead, followed or preceded by providing the particle with at least part of said sample, and
 b) applying an external magnetic field gradient to allow for magnetically controlled motion of said particle on said surface, such that at least part of the sample is streaked onto the solid carrier.

Microbial Sample

As used herein, the term "microbial sample" refers to any sample or specimen known to contain, or suspected to contain, a microorganism or a mixture of microorganisms. Preferably, the microbial sample is a liquid sample.

In one embodiment, it is a culture of microorganisms for reference and research. In order to maintain strains of individual microorganisms, the cultures are usually streaked onto plates containing solidified medium. The inoculum of the culture is generally from a single colony on a previously inoculated plate, and the aim of the streaking procedure is to obtain individual colonies of the strain on the fresh plate. Individual colonies of identical form signify to the worker that a single cell type has been transferred; moreover a single colony serves as the inoculum for further strain transfer and experimentation.

In another embodiment, a microbial sample is a sample for diagnostic microbiological analysis. Diagnostic microbiology is performed in medical, environmental and food testing laboratories and has traditionally used minimal process automation. Conventional laboratory diagnostic microbiology involves specimen collection, registration, inoculation, isolation, identification and testing of pathogenic microbes from clinical specimens. The aim is to obtain isolated colonies of microbes for subsequent analysis.

In a specific embodiment, a microbial sample is a clinical microbial specimen. The isolation and identification of micro-organisms for medical or veterinary diagnostic purposes plays an important role in determining which treatments are required by human or animal subjects with various diseases. Exemplary clinical specimens that are advantageously employed in a method of the invention include urine, upper respiratory swab, genital secretion, sputum, stool, pus, sterile body fluid, and blood culture.

Magnetic Particle

The present invention provides the use of at least one ferromagnetic (also referred to herein as "magnetic" unless indicated otherwise) particle for the transfer, inoculation and/or streaking of a microbial sample. The term "ferromagnetic" as used herein is a broad term and is used in its ordinary sense and includes, without limitation, any material that easily magnetizes, such as a material having atoms that orient their electron spins to conform to an external magnetic field. It is also referred to as "magnetically responsive material." Ferromagnetic materials include materials, such as metals, that are attracted to permanent magnets. Ferromagnetic materials also include electromagnetic materials that are capable of being activated by an electromagnetic transmitter. In one embodiment, the at least one magnetic particle comprises iron, nickel, cobalt or alloys thereof.

The particle may be solid, or semi-solid, e.g. having a hollow core. For example, it comprises a core material covered with a coating material. Factors that may be taken into consideration when choosing a particle material include inertness to microbial sample, resistance to (heat) sterilization, costs, etc. To facilitate efficient coating of the particle with aqueous biological sample, it is preferred that the surface is hydrophilic or at least non-hydrophobic. The particle can be re-used or it can be disposed after use.

Preferably, the particle is a bead. For streaking purposes, a composite bead is used. A bead is an essentially spherical particle. The term "composite" is meant to indicate that the bead is made up of two or more materials, at least one of which is magnetic. Preferably, a composite bead of the invention comprises a magnetic and a non-magnetic material. In one embodiment, the composite bead comprises at least one non-magnetic material, preferably a polymer, and at least one magnetic material. For example, the bead comprises a magnetic core (solid, wire) provided with a polymer coating. The core may have any suitable three dimensional structure. It is for example a solid, spherical core made of a magnetic material. Alternatively, the magnetic core can have a more random structure, such as a tangled wire. In a specific embodiment, the composite bead is a steel bead covered with a hydrophilic material, such as a hydrophilic polymer.

In another embodiment, the bead comprises a polymer core covered with a magnetic coating. Again, any core shape is encompassed. The magnetic coating may comprise particles of one or more magnetic materials, like iron powder.

In yet another embodiment, the bead comprises or consists of a homogeneous mixture of at least non-magnetic material, preferably a hydrophilic polymer, and at least one magnetic material in particulate form, preferably a powder. Very good results were obtained when the relative weight ratio of magnetic material to non-magnetic material is from between 10:90 and 30:70, preferably between 20:80 and 25:75. Any suitable particulate magnetic material may be used. It is for example magnetite, ferrite or a mixture thereof.

Magnetite is a ferrimagnetic mineral with chemical formula $Fe_3O_4$, one of several iron oxides and a member of the spinel group. The chemical IUPAC name is iron(II,III) oxide and the common chemical name ferrous-ferric oxide. The formula for magnetite may also be written as $FeO.Fe_2O_3$, which is one part wüstite (FeO) and one part hematite ($Fe_2O_3$). This refers to the different oxidation states of the iron in one structure, not a solid solution.

Ferrites are a class of chemical compounds with the formula $AB_2O_4$, where A and B represent various metal cations, usually including iron. These ceramic materials are used in applications ranging from magnetic components in microelectronics. Ferrites are a class of spinels, materials that adopt a crystal motif consisting of cubic close-packed (FCC) oxides with A cations occupying one eighth of the octahedral holes and B cations occupying half of the octahedral holes. The magnetic material known as "ZnFe" has the formula $ZnFe_2O_4$, with Fe3+ occupying the octahedral sites and half of the tetrahedral sites. The remaining tetrahedral sites in this spinel are occupied by $Zn^{2+}$.

To allow for heat sterilization of a magnetic particle, it is preferred that the materials used are mechanically resistant up to about the autoclave temperature of 120° C. Other beneficial properties include high chemical resistance, hydrophilicity, mixable with magnetic particulate material, chemical inertness, low costs, and ease to produce. Suitable polymers for use in a composite bead of the invention include epoxy resin, polyamide, polypropylene, and the like.

For mere sample transfer, any three dimensional shape capable of transferring at least part of the sample can be used. It is for example a spherical bead, a rod, an egg-shaped particle, a cubical particle or a particle of undefined three dimensional shape. For an optimal streaking process it is important that the particle can "roll" (rather than slide or slip) on the solid surface along at least one axis of symmetry. accordingly, for the streaking a spherical particle (bead) is used. The streaking or spreading of a sample onto for instance as a glass slide can be accomplished by various means, for instance using a rod or a bead. Especially when streaking for single colonies, an optimal contact surface between particle and solid growth medium is desirable.

The bead diameter can be chosen according to specific circumstances. It may depend on the desired sample volume to be streaked and/or the sample characteristics, such as the (suspected) concentration of microorganism. Suitable beads have a diameter of from about 1 to about 10 mm, preferably 2 to 8. Very good spreading results were obtained with beads having a diameter of 4-6 mm. The density of the bead also influences the spreading properties. For example, if the density is too low the friction with the surface (e.g. an agar culture medium) is not enough to ensure good rolling of the bead. On the other hand, a very high density will damage the agar surface or even sink into the agar when left at a fixed position for a certain time period. Preferably, the density of the bead allows to bead to stay atop of an agar medium for at least 15 seconds, more preferably at least 20 seconds. In one embodiment, the bead density is below about 7 $g/cm^3$, preferably below 5 $g/cm^3$. In a specific aspect, the bead density is less than 4 $g/cm^3$.

The surface of the magnetic particle can be smooth or rough. In one aspect, the at least one magnetic particle has a smooth surface. In a preferred embodiment, especially for streaking purposes, the at least one magnetic particle has a rough surface or at least one cavity for receiving sample. Due to its increased surface area, a rough particle can accommodate a larger sample volume. It can be a magnetic bead with randomly or evenly spaced depressions in its surface, e.g. like a golf ball.

The mean surface roughness of a material can be expressed by the roughness parameters Ra and/or Rz.
Ra=arithmetical mean roughness value
Ra, signifying the roughness parameter, is a value that is recognized and used internationally. It denotes the arithmetical mean value of the absolute values of the profile deviations within the sample area. The numerical value of Ra is always smaller than the Rz reading derived from the same sample.
Rz=mean roughness depth (peak to valley)
Rz denotes the mean roughness depth, i.e. the arithmetical mean of the highest single measurements of several single adjacent tracing sections.

In one embodiment, a magnetic particle for use in the present invention For instance, has a mean surface roughness in the range of Ra=0.1 μm to Ra=25 μm. An Ra value from about 0.1 to about 0.5 μm can be used for only spreading a sample on a surface. An Ra value from about 10 μm to about 25 μm is suitably used for inoculation and spreading since a rough surface picks up a larger inoculum volume. An Ra value of between 2 and 15 μm, such as 5-10 μm is preferred. Suitable Rz values range from between about 10 to about 40 μm, such as 12-30 μm.

In a specific embodiment, a composite bead has a Ra value of about 6 μm and an Rz value of about 25 μm.

The invention also provides a magnetic composite bead suitable for use in a method of the invention. The composite bead, comprising at least one magnetic material and at least one non-magnetic material, like a hydrophilic polymer, may have one or more of the above preferred properties. For example, the invention provides a spherical bead having a magnetic core, a hydrophilic surface, a diameter of 4-6 mm and/or a density of less than 6 $g/cm^3$.

Transfer Method

In a magnetically controlled transfer method of the invention, at least one magnetic particle is used as transport vehicle to transfer at least part of the sample, for instance from transferring a liquid sample from one vial to another, or from a vial to a solid medium. Preferably, multiple particles are used. The particle(s) act(s) as carrier and the amount of sample transferred will depend on the properties of the particle(s) and of the sample. In particular, the size, shape and surface of the particle determine the contact surface and the extent of cohesion with the sample.

The movement of the particle from a first to a second carrier is controlled by a moving magnetic field. As a first step, at least part of said sample associated with a first carrier is contacted with at least one ferromagnetic particle. The term "associated with" is meant to include any type of interaction between the sample and the carrier. For instance, one or more magnetic particle(s) are added to a liquid sample held in a container to absorb or become coated with sample. As another example, a particle is dropped onto a confluent bacterial culture on a culture dish. Optionally, contacting the sample with the particle includes moving the particle in or on the sample. For instance, one or more magnetic beads added to a liquid sample are briefly stirred to homogenize the sample and ensure that a representative portion of the sample becomes associated with the particle. The stirring can be achieved by applying a rapidly changing magnetic field and/or by vortexing. In case a sample is associated with a solid first carrier, the particle may be moved in one or more directions, e.g. by an external magnetic field, to increase the contact surface area between the particle and the sample.

Following contacting the at least one particle with sample, an external magnetic field is used to lift the particle coated with sample out of, or away from, the first carrier and transfer to particle to a second carrier. Thus, the second step involves applying an external magnetic field to allow for magnetically controlled motion of said particle, such that at least part of the sample is transferred to said second carrier. The second carrier can be of any type. It is for instance a liquid culture medium contained in a tube or flask, a solid growth medium, or any solid surface of interest. Again, the magnetic particle may be moved or stirred to maximize sample release from the particle to the second carrier. Following sample release to the second carrier, the particle can be removed or lifted away from the second carrier. It may then be disposed of or it may be sterilized and re-used.

It will be understood that a transfer method according to the invention has endless applications. Specific applications include the preparation of a serial dilution of a stock or concentrated microbial sample. For example, a bacterial inoculum held in a first tube is provided with a magnetic bead. The bead coated with inoculum is transferred by a moving magnetic field into a second tube provided with a liquid broth. After vigorous stirring, the bead is again lifted out of the tube and transferred to a third tube containing a liquid broth. It is of course also possible to leave each bead in the tube and use fresh beads for each transfer. Thereafter, samples may be taken from each tube for further transfer and analysis, e.g. for streaking onto a Petri dish plate using a magnetically controlled streaking method according to the invention. In one embodiment, the invention provides a method for transfer of a microbial sample from a first carrier to a second carrier, the second carrier being a solid carrier, comprising the steps of:
  a) contacting at least part of said sample associated with said first carrier with at least one ferromagnetic particle;
  b) applying a magnetic field gradient to allow for magnetically controlled motion of said particle to said second carrier, such that at least part of the sample is transferred to the surface said second carrier; and
  c) applying a magnetic field gradient to allow for magnetically controlled motion of said particle on said surface, such that at least part of the sample is streaked onto the solid carrier. To allow for optimal streaking performance (see herein above), it is preferred that the at least one ferromagnetic particle is composite bead.

A method of the invention is not limited to sample transfer followed by spreading onto a surface, but is also suitably used for only sample transfer to a solid surface. For analyses typically performed in (medical) micro-biological laboratories, the inoculum is usually spread onto the surface of a solid growth medium. In other sectors, such as the water laboratories it is common to inoculate an empty Petri dish without agar. After inoculation with an aqueous sample, liquid agar is dispensed on the Petri dish. The liquid agar mixes with the sample and co-solidifies.

Streaking Method

A method for streaking a microbial sample onto a solid carrier includes any type of sample spreading or sample streaking on any type of solid surface. For instance, a sample is readily streaked on a glass slide for further analysis, such as Gram staining or visual inspection. In a preferred embodiment, a method is provided for streaking a microbial sample, preferably a clinical specimen, for single colonies.

At least one ferromagnetic composite bead (see herein above) is contacted with a solid surface, the contacting being followed or preceded by providing the particle with at least part of a microbial sample. Streaking of at least part of the sample onto the solid carrier is performed by the application of a moving external magnetic field to allow for magnetically controlled motion of said bead on said surface. In one embodiment, at least one magnetic bead is provided with sample prior to being contacted with the solid surface. For example, a magnetic bead is dropped into or onto a sample to cover its surface with at least part of the sample, followed by transfer or movement of the bead to the solid surface. In fact, this step can be considered as a "transfer method" described above.

In another aspect, at least one magnetic particle is contacted with the solid surface prior to being provided with sample. In an exemplary embodiment, a sample and a particle are deposited in separate steps on a solid surface after which the particle(s) is moved by a magnetic field to spread the sample. The sample may be deposited on or next to the particle, e.g. manually or automatically. After the streaking is completed, the at least one particle can be removed from the solid surface, again using an external magnetic field.

The solid carrier is preferably a solid growth medium contained in a shallow (disposable) dish, like a Petri dish. For microbiology, agar plates are very frequently used. In a specific aspect, the invention provides a method for streaking a microbial sample onto a solid growth medium held in a split-plate Petri dish.

A solid growth medium supports the growth of one or more micro-organisms present or suspected to be present in the sample. Various growth media are known in the art of microbiology. These include so-called selective media, differential media and enriched media.

Selective media are used for the growth of only select micro-organisms. For example, if a micro-organism is resistant to a certain antibiotic, such as ampicillin or tetracycline, then that antibiotic can be added to the medium in order to prevent other cells, which do not possess the resistance, from growing. Selective growth media are also used in cell culture to ensure the survival or proliferation of cells with certain properties, such as antibiotic resistance or the ability to synthesize a certain metabolite. Normally, the presence of a specific gene or an allele of a gene confers upon the cell the ability to grow in the selective medium. In such cases, the gene is termed a marker. Blood agar plates are often used to diagnose infection Differential media or indicator media distinguish one micro-organism type from another growing on the same media. This type of media uses the biochemical characteristics of a micro-organism growing in the presence of specific nutrients or indicators (such as neutral red, phenol red, eosin y, or methylene blue) added to the medium to visibly indicate the defining characteristics of a micro-organism. This type of media is used for the detection of micro-organisms and by molecular biologists to detect recombinant strains of bacteria.

Enriched media contain the nutrients required to support the growth of a wide variety of organisms, including some of the more fastidious ones. They are commonly used to harvest as many different types of microbes as are present in the specimen. Blood agar is an enriched medium in which nutritionally rich whole blood supplements the basic nutrients Magnetic Field Gradient A magnetic field gradient is a variation in the magnetic field with respect to position. Magnetic particles move in the presence of a gradient magnetic field. They thus can be made to move along with the field direction and magnitude. Particles can be navigated or guided e.g. by dragging them using one or more external sweeping permanent magnets. A one-dimensional magnetic field gradient is a variation with respect to one direction, while a two-dimensional gradient is a variation with respect to two, and so on. The magnetic field can vary in intensity and/or direction and can be achieved by mechanically varying the positions of one or more magnets with respect to the particle. Suitable magnets include both permanent magnets and electromagnets. Commercially available permanent magnets include magnetic metallic elements, composites such as ceramics and ferrites, and rare earth magnets. Electromagnets are also commercially available.

In a preferred embodiment, applying a magnetic field gradient comprises the use of an electromagnetic field. The core of the electromagnet preferably has a high permittivity to achieve a high field strength using low electro power.

A specific aspect relates to the use of a grid or array of multiple small electromagnets to apply a magnetic field gradient, typically in a predetermined pattern. The strength and direction of the magnetic field gradient control the direction and/or magnitude determines the path, lengths, intensity and/or pattern of particle motion. For instance, a magnetic bead coated with sample can be lifted out of a tube by an electromagnet placed next to the tube to pick up the bead, followed by an upward movement of the magnet that is followed by movement of the bead. The bead can then be transferred to any desired destination while being held by the magnet. Upon arrival at the desired destination, the bead may simply be released from the magnet by switching off the magnetic field.

The skilled person will be able to determine the optimal magnetic field strength for a specific situation. When inoculating and/or streaking a solid growth medium, the field strength has to be as high as possible as long as the magnetic particle does not damage the medium. In one embodiment wherein one or more beads are used for sample spreading onto agar, the magnetic field only produces a horizontal force on the bead(s) and no vertical force, resulting in rolling of the bead(s) without damaging the agar.

Moving the bead can for instance be achieved by using a permanent Neodymium (NdFeB) magnet with a surface field strength of 0.7 T (tesla) and a diameter of 6 mm by 3 mm height. The field strength decreases rapidly further away from the magnet. The distance between the magnetic particle and the magnet may be minimized in view of the field strength and/or the accuracy of the magnetically controlled motion. The one or more magnets are for instance placed essentially directly (e.g. with a spacing of only 0.5 to 5 mm) below the Petri dish. In a streaking method provided herein, the external magnetic field gradient can make the at least one magnetic particle to follow a zig-zag pattern, a concentric pattern, a four quadrant pattern or an at random pattern on the surface of a solid carrier (see FIG. 2).

Container

To detect micro-organisms, e.g. bacteria, in clinical samples, a specimen can be collected from the infected site using a swab which is then inserted into a transport container. Samples from urine and other fluids are collected in proper vials.

A further aspect of the invention relates to a container suitable or designed for receiving or collecting a microbial sample, said container comprising at least one magnetic particle. In one embodiment, the container is a disposable container, preferably a disposable test-tube or vial. Preferably, the container can receive a liquid sample, for instance a liquid microbial sample, a liquid transport medium and/or a liquid growth medium. It may be provided with a removable cap. Exemplary containers include devices for collecting, transporting and/or storing biological specimens. The at least one magnetic particle present in the container is advantageously used to homogenize and/or transfer the microbial sample held in the container.

In one embodiment, the container comprises in addition to one or more magnetic particles, a liquid transport medium or a liquid culture medium. Such a container is advantageously used as collection device in a culture swab system. Alternatively, or additionally, it may contain a swab for collecting a microbial sample (see e.g. WO2004/086979). An ideal culture swab system must have the ability to absorb organisms from the site of infection, to maintain the viability of organisms during transport and prior to plating, and finally, to allow the release of organisms from the swab onto the appropriate media. These are all critical aspects to be considered when choosing the most appropriate collection device. The magnetic particles in a container of the invention can assist the release of sample from the swab prior to analysis. The container comprising a microbial sample is advantageously subjected to a transfer or streaking method as provided herein.

The invention also relates to an apparatus suitable for use in a method according to the invention, said apparatus comprising a culture dish loading station, a sampling unit for applying or inoculating sample onto a culture dish, a streaking mechanism and a computer control system, characterized in that the sampling unit and/or said streaking mechanism are provided with at least one magnet for generating a magnetic field gradient and wherein the control system is connected to said at least one magnet.

In a specific aspect, the invention provides an apparatus for automated or semi-automated high-throughput streaking of a microbial sample by making use of a magnetic field gradient. The apparatus preferably contains multiple inoculation and spreading positions to allow for parallel processing of multiple samples. Automated streaking systems per se are known in the art. Typically, they comprise a culture dish loading station, a sampling unit for applying or inoculating a sample onto a culture dish, a streaking mechanism and a computer control system for controlling the elements of the apparatus. In one embodiment, an apparatus according to the present invention is characterized in that the sampling unit, and preferably also the streaking mechanism, comprises at least one magnet for generating a magnetic field gradient and a control system connected to said at least one magnet, in order to magnetically control inoculation and preferably also the streaking of a culture dish. Accordingly, the invention provides an apparatus suitable for conducting a method according to claim 1 and those depending thereon in an automated or semi-automated fashion, said apparatus comprising a culture dish loading station, a sampling unit for applying or inoculating sample onto a culture dish, a streaking mechanism and a computer control system, characterized in that said sampling unit, and optionally also said streaking mechanism, is/are provided with at least one magnet capable of generating a magnetic field gradient and wherein the control system is connected to said at least one magnet.

In another embodiment, the invention provides a streaking apparatus for conducting a streaking method according to claim 2 in an automated or semi-automated fashion, the apparatus comprising a culture dish loading station, a sampling unit for applying or inoculating sample onto a culture dish, a streaking mechanism and a computer control system, wherein said streaking mechanism is provided with at least one magnet capable of generating a magnetic field gradient and wherein the control system is connected to said at least one magnet, said apparatus further comprising a magnetic particle dispensing unit comprising a plurality of magnetic composite beads.

Such an apparatus provides a versatile system for varying the streaking procedure, e.g. in accordance with the sample to be streaked. These patterns can provide an increasing dilution of the sample and are effected by a magnetically controlled streaking tool. Once so streaked, the prepared dishes can then be incubated to promote growth of one or more micro-organisms. The growth can then be examined or subjected to further tests for isolation and/or identification of the micro-organism type(s) present in the specimen.

An apparatus provided herein has several advantages over the known automated streaking systems known in the art. It is more flexible with respect to both the specimen type and the type of carrier to which sample is transferred or spread (e.g. regular Petri dish, miniature Petri dish, split-type Petri dish, glass slide, culture tube). Different sizes of particles can be used for different application. Within an apparatus, the magnetic particles are easy to apply to and remove from one carrier to another due to magnetic control. For reasons explained herein above, magnetic composite beads are preferred. The particles can be reused after sterilization. Using magnetic field gradients, an endless number of different streaking patterns can be programmed, and these can be readily changed in between samples. The use of several magnets capable of inducing a magnetic field gradient allows for the processing of many samples simultaneously. The overall capacity of a magnetically controlled streaking apparatus can be very high; up to 3- or even 4-fold higher as compared to the best performing apparatus presently available on the market.

An apparatus of the invention preferably comprises a conveyor system for transporting and handling containers with specimen (e.g. a tube with urine or a swab) into the apparatus. The containers may be grasped manually or by an automated manipulating device and move it to a desired position, for example next to the culture dish it must be streaked on. The manipulating device may be designed to remove a cap from the container. According to the invention, sample inoculation onto multiple carriers, e.g. a Petri dish, a tube containing liquid growth broth and a glass slide, can be performed in a single process step, for example using proportional pipetting.

In the sampling unit, sample can be transferred from the container to a carrier, like a culture dish, in an automated fashion. In one embodiment, the container with specimen is a container according to the present invention, comprising at least one magnetic particle, such as one or more magnetic (composite) beads. By adding magnetic particles to a sample in liquid phase, for example urine or to a tube with a swab inserted into liquid transport medium, culture dishes can be inoculated and spread using the same underlying principle. i.e. through magnetically controlled motion of one or more magnetic particles. This omits the use of swabs and inoculating loops.

The control system of the apparatus can be programmed to produce a magnetic field gradient that allows for magnetically controlled transfer of sample according to a 'transfer method' provided herein. Thus, the sampling unit may comprise one or more magnets to allow for 1) retrieval of at least one magnetic particle carrying sample from a specimen container, and 2) transfer of said particle and associated sample to a deposit location on a culture dish. The specimen container may then be provided again with the cap. However, while the container is uncapped, it may be convenient to transfer sample not only to a culture dish, but also to other types of carriers, such as a glass slide or a liquid broth. The apparatus may thus also provide for a slide dispensing unit and/or a tube dispensing unit.

Once a sample is transferred to the culture dish, e.g. by means of magnetically controlled motion of a particle provided with sample, streaking is effected in the streaking unit of the apparatus. Said streaking unit is controlled by the computer control system. If the streaking mechanism is provided with at least one magnet, it provides for magnetically controlled streaking bacterial samples in programmable patterns to produce isolated bacterial colonies.

The apparatus may also provide for other means known in the art to be of use in automated sample handling and/or streaking, for example one or more of the elements described in WO2005/071055 other than the specific "comb-like" streaking device mentioned therein. These include culture plate lid removal means to remove and replace a lid of the culture plates to be streaked. Other useful elements of an apparatus include a sample identification unit, preferably capable of reading barcodes on a specimen container.

An apparatus of the invention may be used as follows:
1. a barcoded sample is scanned so the apparatus knows which Petri dishes/tube/slice needs to be inoculated. The required Petri dishes are requested.
2. The Petri dishes arrive at the sampling unit in the correct order.
3. automated lid removal means takes the lid of the dishes
4. a slide dispensing unit and a tube dispensing unit present the required slides and tubes at the sampling unit.
5. a laboratory worker takes the sample and manually inoculates the Petri dishes, slices and tubes.
6. a magnetic particle dispensing unit places at least one magnetic composite bead at a predetermined location on the Petri dish
7. the lid is replaced onto the dish and the dish is moved to the streaking mechanism
8. a magnetic field gradient is applied to spread the sample onto the solid growth medium in the Petri dish in a desired pattern according to the sample.
9. After removing of the bead the plates are removed from the streaking mechanism and transported to the incubators to promote growth of micro-organisms.

Figure 1A:
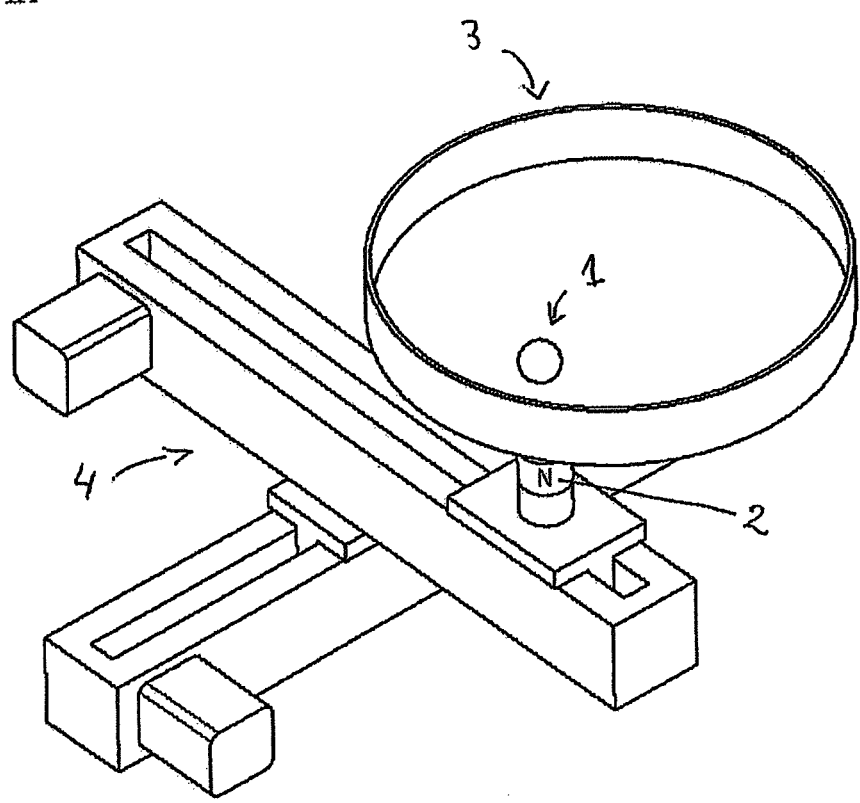
FIG. 1 shows schematic perspective views of a solid carrier provided with a magnetic particle. Sample is not included in the drawings. Illustrates are various embodiments wherein a two-dimensional magnetic field gradient may be used to control the motion of a magnetic particle, in this case a magnetic bead on the surface of a solid carrier, e.g. a growth medium contained in a Petri dish. In panels B and C, a section of the Petri dish has been cut away to better illustrate the position of the external magnet(s).
Figure 1B:
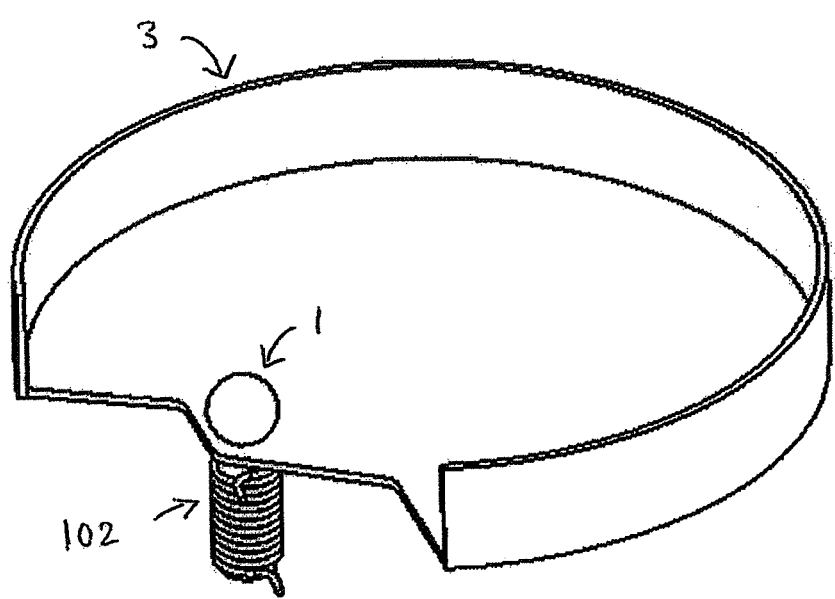
Figure 1C:
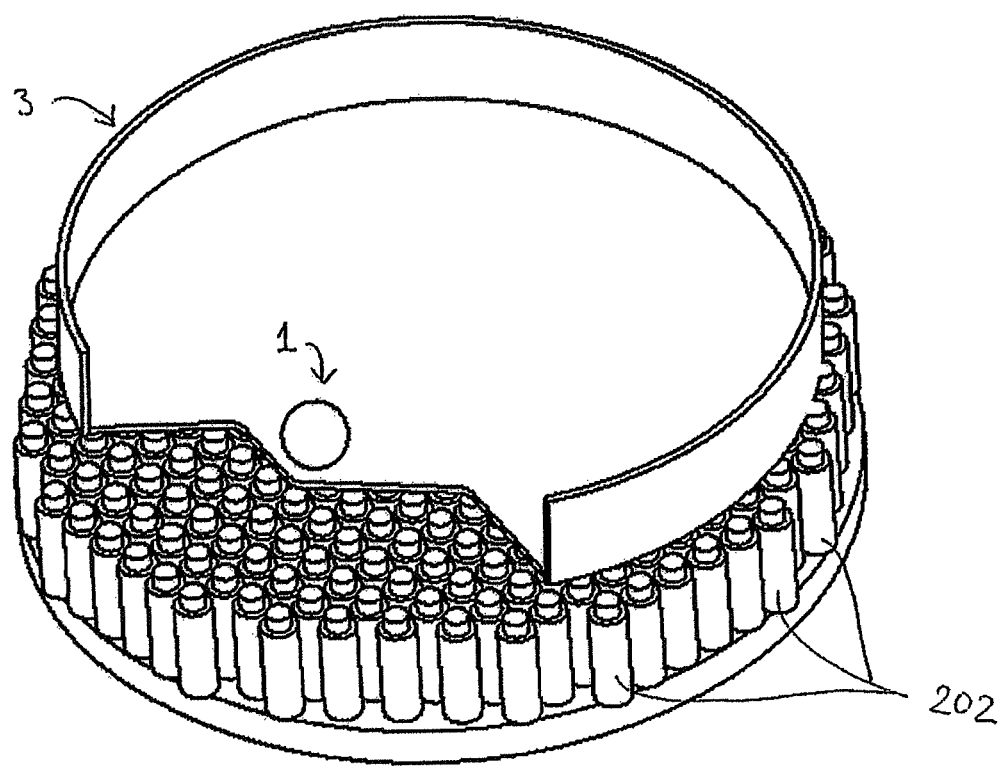

In panel A, the movement of a magnet particle 1 on the surface of dish 3 is controlled through a magnetic field gradient generated by permanent magnet 2 attached to a movement mechanism 4, capable of moving the magnet in the x- and/or y-direction. The movement mechanism may be controlled by software to generate a magnetic field gradient to create the desired streaking pattern.

In panel B, the magnetic bead 1 is moved across the agar surface by use of a controllable electromagnet 102. The electromagnet 102 is positioned just below the Petri dish 3. The magnet can be moved using the mechanism shown in panel A.

In panel C, the movement of the magnetic bead 1 is controlled through a grid of multiple adjacent electromagnets 202. The electromagnet grid moves the bead through switching the magnets on and off in controlled pattern and order, thereby generating a magnetic field gradient. Herewith, the bead can be moved on the surface of dish 3 without the need of a movement mechanism having movable parts.

Figure 2:
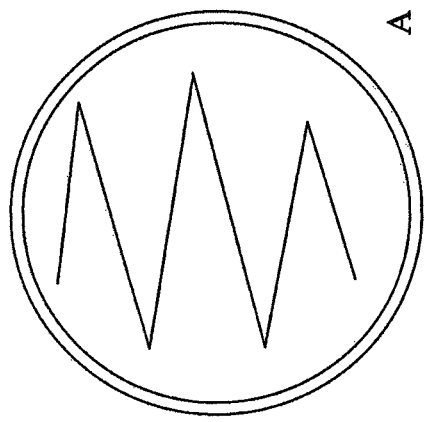
Figure 2:
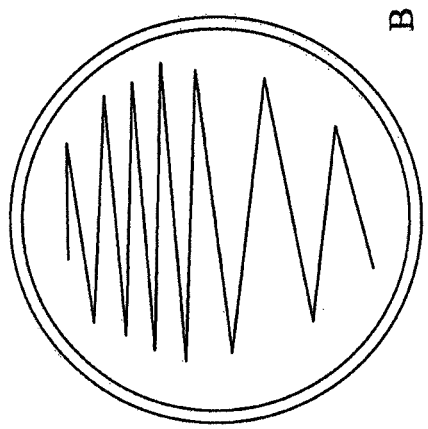
Figure 2:
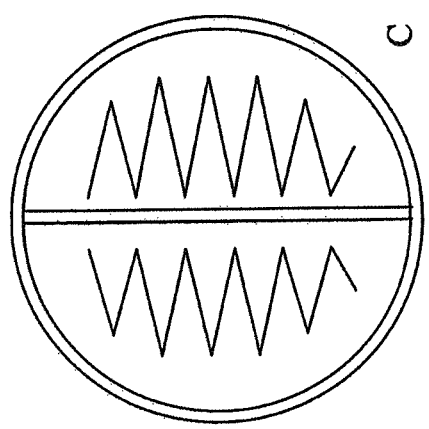
Figure 2:
Figure 2:
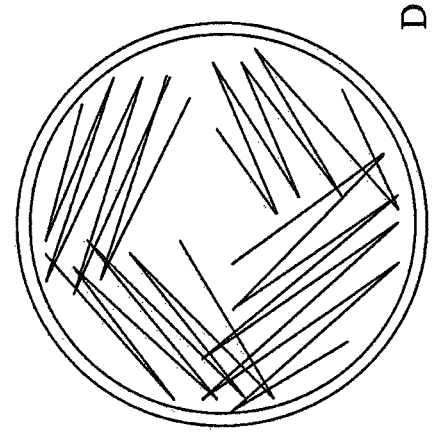
Figure 2:
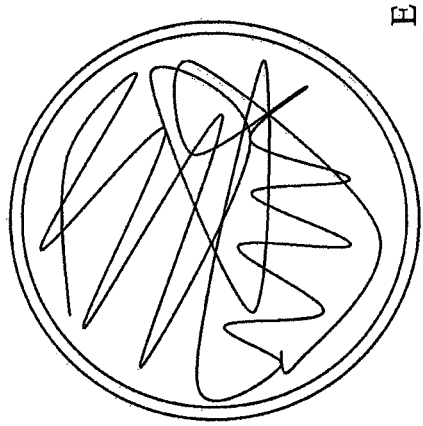
Figure 3:
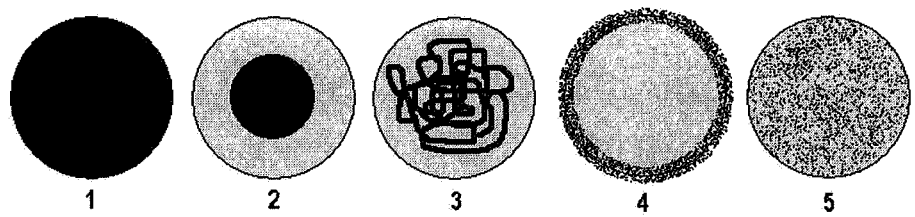

FIG. 2 shows schematic drawings of exemplary streaking patterns that can be obtained using a method of the invention.
Panel A: zig-zag streak pattern on whole plates extensive
Panel B: zig-zag streak pattern on whole plates intensive during first half of the plate and then extensive on second half of the plate
Panel C: zig-zag streak pattern on split-plate
Panel D: four quadrant streak pattern on whole plate
Panel E: at random movement
Panel F: streak on glass slide FIG. 3 shows schematic drawings of the cross-section of the various beads used in Example 2. Bead number 1 is a non-composite steel bead known in the art. Beads 2-5 represent composite beads according to the invention. For details see Example 2.

EXAMPLES

Example 1

Experiments were performed to assess the performance of the magnetically controlled spreading technique according to the invention as compared to the conventional spreading technique using a plastic inoculating loop.

Ten (10) μl of a bacterial suspension containing *E. coli* was applied in the middle of a Petri dish containing solid blood agar growth medium. One plate was streaked with an inoculating loop in the typical zig-zag streak pattern. To the second plate, a magnetic bead was applied onto the inoculated sample. A permanent magnet was placed under the Petri dish and the magnet was moved manually such that the bead was moved onto the solid surface of the growth medium in a zig-zag streak pattern similar to that of the first plate. Following streaking, the bead was removed by the application of a magnetic force. The plates were incubated for 24 hours at 37° C. to allow for growth of *E. coli* colonies.

Visual inspection of the plates after the incubation period revealed that the results of the second plate were superior in the sense that the final streak produced more single isolated colonies. Conceivably, this is due the facts that the beads are rolling while spreading the bacteria onto the solid medium, providing a better sample dilution than what can be obtained using conventional loops. Similar advantages of the bead-mediated spreading were observed for the different bacterial strain (*S. saprophyticus*) and with a different streaking pattern.

Example 2

Magnetic Bead Properties

1. Bead Materials

The principle of spreading with a bead relies on a magnetic bead/particle. It is clear that at least one material in the bead should be magnetic or capable of being influenced by a magnet. It was discovered that the bead must roll in order to achieve a good spreading result. A bead that is a magnet by itself is therefore not usable. Also a ferromagnetic bead which forms a dipole is not usable. The spreading performance of various composite beads (numbers 2-5; see FIG. 3) was determined and compared with a non-composite stainless steel bead (number 1) used in the prior art streaking methods and devices.

1. Non-composite: a massive stainless steel bead (comparative example).
2. Composite (Massive core coated with polymer): a small stainless steel bead is covered with epoxy to let it roll better.
3. Composite (Wire core coated with polymer): Steel wire is folded to a globular shape, the surface is created with epoxy.
4. Composite (Polymer core coated with magnetic material): An epoxy bead is covered with a layer of iron particles.
5. Composite (Homogenous mixture of magnetic and non-magnetic material): epoxy is mixed with iron particles.

Test Results

In the table below a summary of the test results are visible. The beads are judged by the following points.
Bead number: construction and materials of the bead, see above.
Rolling: quality of rolling
Sample pick up: The total inoculated sample volume that can be picked up by the bead.
Single colonies: Amount of single colonies on an agar plate, an indicator for the quality of the bacterial spread on the plate.
Speed: The speed of the spreading that can be reached.

The points to scored range between – and ++. To determine the total amount all the "+" are counted. A "–" subtracts a point and "+/–" means no points.

TABLE 1 test results obtained with non-composite beads versus various types of composite beads.

| Bead number | Rolling | Sample pick-up | Single colonies | Speed | Total |
|---|---|---|---|---|---|
| 1 | – | + | – | + | 0 |
| 2 | +/– | ++ | + | +/– | 3 |
| 3 | + | ++ | ++ | + | 6 |
| 4 | +/– | + | + | – | 1 |
| 5 | ++ | ++ | ++ | + | 7 |

The surface of the beads determines among others the quality of the spreading, because the surface is responsible for picking up and losing the bacteria. The beads with a polymer coating on the outside gives the best spreading result, whereas the beads with iron on the outside gives a poorer spread. The polymer surface has a greater roughness, so it will pick more sample.

There are two main points that determine the rolling of the bead;
The surface roughness gives resistance with the agar. Through the resistance the bead will encounter a force that will let it roll.
The properties of the magnetic material. The magnetic properties are responsible for two forces:
1. The forming of a dipole, the dipole will try to stay aligned with the magnet under the dish
2. The magnetic field will introduce eddy currents in the metal leading to a moment opposed to the direction of movement. This force is only present if the beads roll, it will slow the bead down but will not prevent rolling.

As long as the force from the resistance is higher than the 2 magnetic forces combined, the bead will roll. A preferred magnetic core for the bead is made of a material that has no magnetic dipole and eddy currents. This is a material with very low demagnetization forces, divided into small particles (the smaller the particles the smaller the eddy currents). Powdered magnetic material is suitably used for this purpose.

The massive stainless steel bead known in the art has too high magnetic forces and will roll poorly or not at all. The wire bead (no. 4) and the powder mixed bead (no. 5) give the best results. However, the mixed powder bead is much easier to produce.

Filler Material.

To determine the suitable amount of iron particles in the bead, the following beads were made

| 0.1 gram iron, | 60% mass, | 21% volume |
| 0.2 gram iron, | 80% mass, | 42% volume |
| 0.3 gram iron, | 90% mass, | 63% volume |

The beads with 0.3 gram iron are difficult to produce. The amount of filler material his a slight influence on the spreading quality and a slight influence on the spreading speed. With higher amounts of iron the reachable spreading speed is higher. The most optimum amount of iron is 0.2 gram. A bead with 0.2 gram iron powder was therefore used for further testing.

2. Bead Density

Besides the rolling properties, the weight of the bead is also important. The weight determines the time the bead can lay on the agar without sinking. During the automated spreading, it is possible that the bead stays on the same spot for 20 seconds or even longer. The test results obtained with various types of beads are given in Table 2:

TABLE 2

Effect of bead diameter and bead type on sinking into solid agar.

| Bead diameter (mm) | Bead type (see Table 1) | Time without sinking (sec) |
|---|---|---|
| 5 | 1 | 10 |
| 5 | 3 | 17 |
| 5 | 5 | 25 |
| 7 | 1 | 15 |
| 7 | 3 | 27 |
| 7 | 5 | 40 |

The massive steel bead sinks into the agar too fast. The larger polymer-covered wire bead (no. 3) can reach 20 seconds without sinking. The bead made of polymer mixed with iron powder can stay on the agar for more than 20 seconds, irrespective of the size.

The densities of the materials used are:

| Type 1 | 7.2 g/cm$^3$ |
| Type 3 | 4.3 g/cm$^3$ |
| Type 5 | 3.9 g/cm$^3$ |

These data, combined with the sinking results of table 2 indicate that a bead material most preferably has a density below 4.0 g/cm$^3$.

3. Bead Size

The bead size has a major influence on the spreading itself; it has a minor influence on the bacterial growth result of the spreading. With most bead sizes, e.g. between 4 and 7 mm, good bacterial growth results are achieved. The quality of the bacterial growth is determined on the amount of single colonies, the more single colonies there are on a plate, the better.

TABLE 3

Effect of bead diameter on spreading performance.

| Bead size | Speed | Sample pick-up | Single colonies | Sensitivity | Total |
|---|---|---|---|---|---|
| 3 | + | +/− | +/− | − | 0 |
| 4 | ++ | + | + | +/− | 4 |
| 5 | ++ | ++ | ++ | + | 7 |
| 6 | + | ++ | ++ | + | 6 |
| 7 | + | + | ++ | ++ | 6 |
| 8 | +/− | + | + | ++ | 4 |

Legend

Bead size: the diameter of the beads in mm.
Speed: the reachable speed of the spreading.
Sample pick up: The amount the total inoculated sample that can be picked up by the bead
Single colonies: Amount of single colonies on an agar plate
Sensitivity: How difficult is it to stop the bead from spreading through imperfectness on the agar surface (e.g. bumps, holes, slimy sample)

4. Bead Surface

The surface of the bead is responsible for the rolling and spreading of the sample. The influences on the rolling is discussed in the previous chapter.

Sample Spreading

The surface roughness influences the amount of sample that can be picked up by the bead. The sample forms a film around the bead. The larger the surface area, the more sample can be provided onto the bead.

Roughness

Highly suitable beads have the following roughness:

| VDI 36: | Ra | 6.30 µm |
| | Rz | 24.0 µm |

(VDI is a roughness indicator used in the mould making industry, especially in Germany. Ra and Rz values are international recognized units for surface roughness.)

Hydrophilic/Hydrophobic

The bead surface must be capable of attracting or adsorbing the sample. Almost all biological samples have water as main component. Therefore it is preferred that the bead surface has a hydrophilic character.

5. Production Bead

Materials

For the testing of Type 5 composite beads, a homogenous mixture of home made iron powder and epoxy was used. These materials are not very suitable for mass production. Commercially available magnetic filler materials can be combined with several polymers include magnetite and ferrite. The melted polymer+magnetic particles must flow into a moulding cavity to make the bead. The particle size of the magnetic material in particulate form has a significant impact on the flow rate and on the quality of the produced bead. Preferably it should be as small as possible. Powdered magnetic materials are preferred.

Magnetite. It is a ceramic material and therefore resistant against al forms of corrosion.

Properties

| Material | Fe₃O₄ |
|---|---|
| Density | 5.17 g/cm³ |
| Chemical Resistance | very high |

Ferrite:
Properties

| Material | Fe |
|---|---|
|  | Maximal 0.05% of other materials |
| Density | 5.17 g/cm³ |

The polymer used for binding the magnetic particles/powder may be selected based on the following properties
High chemical resistance
Mixable with Magnetite and Ferrite
Mechanical strength up to 120 degrees Celcius (autoclave temperature)
Contains no chemicals ore parts that can come out of the material into the sample.
Low cost price and easy to produce.
The material used for testing is

| Material | PA, Polyamide (nylon) |
|---|---|
| Density | 1.39-1.58 g/cm³ |
| Tensile strength | 70-120 MPa |
| Useful temp range | −50-120° C. |
| Melting Temp. (range) | 216 |
| Hardness | 92 Rockwell (E Scale) |
| Chemical Reactivity | low |
| Chemical Resistance | high |

Other Possibilities are
Common thermoplastic materials which meet the requirements as stated above.

Example

| Material | PP, Polypropylene |
|---|---|
| Density | 0.90 g/cm³ |
| Tensile @ Yield | 23 MPa |
| Softening Temp. | 143° C. |
| Melting Temp. (range) | 160° C.-166° C. |
| Hardness | 66 Rockwell (R Scale) |
| Chemical Reactivity | low |
| Chemical Resistance | high |

The amount of polymer in comparison to the amount magnetic material is:
20-25% polymer (binding)
75-80% magnetic material (magnetic strength)

The invention claimed is:

1. A method for streaking a microbial sample onto a solid carrier, comprising:
providing a microbial sample;
providing at least one ferromagnetic particle optionally formed as a composite bead, wherein the particle or bead has a surface roughness (Ra) in the range of 0.1 to 25 µm, a diameter of between 2 to 8 mm and a density below 7 g/cm³;
contacting a surface of said solid carrier with the particle;
providing the particle with at least part of said sample; and
applying a magnetic field gradient to allow for magnetically controlled motion of said particle on said surface in a predetermined pattern controlled by the magnetic field gradient, such that at least part of the sample is streaked onto the solid carrier wherein the solid carrier remains stationary while the sample is streaked onto the solid carrier by the magnetically controlled motion of the particle using the magnetic field gradient.

2. The method of claim 1, wherein said carrier is selected from the group consisting of a glass slide, and a solid culture medium contained in culture plate.

3. The method of claim 1, wherein said microbial sample is a clinical specimen.

4. The method of claim 3, wherein the clinical specimen is selected from the group consisting of urine, an upper respiratory swab, a genital secretion, sputum, stool, pus, a sterile body fluid, a blood culture, and combinations of any thereof.

5. The method of claim 1, wherein the particle has a surface roughness of between 2 and 15 µm.

6. The method of claim 5, wherein the particle has a surface roughness of between 5 and 10 µm.

7. The method of claim 1, wherein said particle comprises a hydrophilic surface.

8. The method of claim 1, wherein said particle comprises at least one polymer and at least one magnetic material.

9. The method of claim 8, wherein the particle comprises a magnetic core comprising a polymer coating.

10. The method according of claim 8, wherein the particle comprises a polymer core comprising a magnetic coating.

11. The method of claim 8, wherein the particle is made of a homogeneous mixture of at least one polymer and at least one magnetic material in particulate form.

12. The method of claim 11, wherein the particle is made of a homogeneous mixture of at least one polymer and at least one magnetic powder.

13. The method of claim 8, wherein the relative weight ratio of magnetic material to polymer is from between 10:90 and 30:70.

14. The method of claim 13, wherein the relative weight ratio of magnetic material to polymer is from between 20:80 and 25:75.

15. The method of claim 1, wherein the particle is comprised of a material selected from the group consisting of magnetite, ferrite, and combinations of any thereof.

16. The method of claim 1, wherein the particle comprises a polymer that is heat resistant up to 120° C.

17. The method of claim 16, wherein the particle comprises a polymer selected from the group consisting of an epoxy, a polyamide, a polypropylene, and combinations of any thereof.

18. The method of claim 1, wherein the particle diameter is from 3-8 mm.

19. The method of claim 18, wherein the particle diameter is from 4-6 mm.

20. The method of claim 1, wherein the particle density is less than 5 g/cm³.

21. The method of claim 20, wherein the particle density is less than 4 g/cm³.

22. A method for streaking a microbial sample onto a solid carrier, comprising:
providing a microbial sample;
providing at least one ferromagnetic particle optionally formed as a composite bead, wherein the particle or bead has a surface roughness (Ra) in the range of 0.1 to 25 µm, a diameter of between 2 to 8 mm and a density below 7 g/cm³;
contacting a surface of said solid carrier with the particle;

providing the particle with at least part of said sample; and
applying a magnetic field gradient provided by a grid of
   multiple adjacent electromagnets to allow for magnetically controlled motion of said particle on said surface in
   a predetermined pattern controlled by the magnetic field
   gradient, such that at least part of the sample is streaked
   onto the solid carrier wherein the solid carrier remains
   stationary while the sample is streaked onto the solid
   carrier by the magnetically controlled motion of the
   particle using the magnetic field gradient provided by
   the grid.

* * * * *